(12) United States Patent
Cappello et al.

(10) Patent No.: US 10,322,238 B2
(45) Date of Patent: *Jun. 18, 2019

(54) NEEDLE-FREE INTRADERMAL INJECTION DEVICE

(71) Applicant: PHARMAJET INC., Golden, CO (US)

(72) Inventors: Chris Cappello, Golden, CO (US); Matt Wixey, Golden, CO (US); John W. Bingham, Golden, CO (US)

(73) Assignee: PharmaJet, Inc., Golden, CO (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/644,951

(22) Filed: Jul. 10, 2017

(65) Prior Publication Data

US 2017/0304543 A1    Oct. 26, 2017

Related U.S. Application Data

(63) Continuation of application No. 15/235,797, filed on Aug. 12, 2016, now Pat. No. 9,700,675, which is a
(Continued)

(51) Int. Cl.
*A61M 5/30* (2006.01)
*A61M 5/20* (2006.01)

(52) U.S. Cl.
CPC ............ *A61M 5/30* (2013.01); *A61M 5/20* (2013.01); *A61M 2005/2013* (2013.01)

(58) Field of Classification Search
CPC ................................ A61M 5/20; A61M 5/30; A61M 2005/2013
See application file for complete search history.

(56) References Cited

U.S. PATENT DOCUMENTS

| 569,887 A | 10/1896 | Richardson |
| 2,547,099 A | 4/1951 | Smoot |

(Continued)

FOREIGN PATENT DOCUMENTS

| CA | 569887 | 2/1959 |
| EP | 1 093 826 | 4/2001 |

(Continued)

OTHER PUBLICATIONS

International Search Report dated Jun. 15, 2006, for PCT Patent Application No. PCT/US05/46041 filed on Dec. 20, 2005, one page.
(Continued)

*Primary Examiner* — Imani N Hayman
*Assistant Examiner* — Tiffany Legette
(74) *Attorney, Agent, or Firm* — Adsero IP

(57) ABSTRACT

A needle-free injection device suitable for delivering a therapeutic substance into the intradermal space of a patient. The needle-free injection device includes an injector body defining a syringe end. The device also includes a first handle attached with a hinge to the injector body such that the first handle pivots between an open and a closed position and remains attached to the injector body during an injection, a main spring positioned within the injector body, a return sleeve engaged with the main spring, and a first linkage between the first handle and the return sleeve. The first linkage causes the return sleeve to move away from the syringe end of the injector body when the first handle is moved from the open position to the closed position, thereby compressing the main spring. Needle-free injection systems and methods of operating a needle-free injection device are also disclosed.

18 Claims, 13 Drawing Sheets

Related U.S. Application Data continuation of application No. 13/711,765, filed on Dec. 12, 2012, now Pat. No. 9,433,735.

(60) Provisional application No. 61/570,163, filed on Dec. 13, 2011.

(56) References Cited

U.S. PATENT DOCUMENTS

| | | |
|---|---|---|
| 2,605,763 A | 8/1952 | Smoot |
| 2,635,601 A | 4/1953 | May |
| 2,645,223 A | 7/1953 | Lawshe et al. |
| 2,687,724 A | 8/1954 | Ziherl et al. |
| 2,699,166 A | 1/1955 | Dickinson, Jr. et al. |
| 2,704,542 A | 3/1955 | Scherer |
| 2,704,543 A | 3/1955 | Scherer |
| 2,737,946 A | 3/1956 | Hein, Jr. |
| 2,764,977 A | 10/1956 | Ferquson |
| 2,800,903 A | 7/1957 | Smoot |
| RE24,419 E | 1/1958 | Ziherl et al. |
| 2,821,193 A | 1/1958 | Ziherl et al. |
| 2,821,981 A | 2/1958 | Ziherl et al. |
| 3,057,349 A | 10/1962 | Ismach |
| 3,115,133 A | 12/1963 | Morando |
| 3,131,692 A | 5/1964 | Love |
| 3,138,157 A | 6/1964 | Ziherl et al. |
| 3,202,151 A | 8/1965 | Kath |
| 3,292,621 A | 12/1966 | Banker |
| 3,292,622 A | 12/1966 | Banker |
| 3,335,722 A | 8/1967 | Lowry et al. |
| 3,424,154 A | 1/1969 | Kinsley |
| 3,461,867 A | 8/1969 | Zimmet et al. |
| 3,507,276 A | 4/1970 | Burgess |
| 3,540,444 A | 11/1970 | Moreland |
| 3,688,765 A | 9/1972 | Gasaway |
| 3,695,266 A | 10/1972 | Lussier |
| 3,714,943 A | 2/1973 | Yanof et al. |
| 3,763,359 A | 10/1973 | Cho et al. |
| 3,763,859 A | 10/1973 | Yanof et al. |
| 3,782,380 A | 1/1974 | Van Der Gaast |
| 3,788,315 A | 1/1974 | Laurens |
| 3,805,783 A | 4/1974 | Ismach |
| 3,815,594 A | 6/1974 | Doherty |
| 3,853,125 A | 12/1974 | Clark et al. |
| 3,859,996 A | 1/1975 | Mizzy et al. |
| 3,908,651 A | 9/1975 | Fudge |
| 3,933,155 A | 1/1976 | Johnston |
| 3,945,379 A | 3/1976 | Pritz et al. |
| 3,945,383 A | 3/1976 | Bennett et al. |
| 4,004,575 A | 1/1977 | Sarstedt |
| 4,031,889 A | 6/1977 | Pike |
| 4,059,107 A | 11/1977 | Iriquchi et al. |
| 4,089,334 A | 5/1978 | Schwebel et al. |
| 4,103,684 A | 8/1978 | Ismach |
| 4,124,024 A | 11/1978 | Schwebel |
| 4,128,098 A | 12/1978 | Bloom et al. |
| 4,301,795 A | 11/1981 | Zimmerman |
| 4,329,988 A | 5/1982 | Sarnoff et al. |
| 4,342,310 A | 8/1982 | Lindmayer et al. |
| 4,400,172 A | 8/1983 | Dettbarn et al. |
| 4,403,609 A | 9/1983 | Cohen |
| 4,403,989 A | 9/1983 | Christensen et al. |
| 4,421,508 A | 12/1983 | Cohen |
| 4,447,225 A | 5/1984 | Taff et al. |
| 4,475,905 A | 10/1984 | Himmelstrup |
| 4,507,113 A | 3/1985 | Dunlap |
| 4,518,385 A | 5/1985 | Lindmayer et al. |
| 4,592,742 A | 6/1986 | Landau |
| 4,596,556 A | 6/1986 | Morrow et al. |
| 4,616,650 A | 10/1986 | Green et al. |
| 4,680,027 A | 7/1987 | Parsons et al. |
| 5,106,371 A | 4/1992 | Zhao et al. |
| 5,211,628 A | 5/1993 | Marshall |
| 5,312,335 A | 5/1994 | McKinnon et al. |
| 5,312,348 A | 5/1994 | Sans |
| 5,397,313 A | 3/1995 | Gross |
| 5,415,255 A | 5/1995 | Hafner |
| 5,499,972 A | 3/1996 | Parsons |
| 5,503,627 A | 4/1996 | McKinnon et al. |
| 5,527,284 A | 6/1996 | Ohnemus et al. |
| 5,531,705 A | 7/1996 | Alter et al. |
| 5,556,384 A | 9/1996 | da Encarnacao |
| 5,569,181 A | 10/1996 | Parsons |
| 5,569,189 A | 10/1996 | Parsons |
| 5,569,203 A | 10/1996 | Chen |
| 5,575,774 A | 11/1996 | Chen |
| 5,578,015 A | 11/1996 | Robb |
| 5,599,302 A | 2/1997 | Lilley et al. |
| 5,620,423 A | 4/1997 | Eykmann et al. |
| 5,649,912 A | 7/1997 | Peterson |
| 5,704,911 A | 1/1998 | Parsons |
| 5,782,802 A | 7/1998 | Landau |
| 5,865,795 A | 2/1999 | Schiff et al. |
| 5,891,086 A | 4/1999 | Weston |
| 5,899,879 A | 5/1999 | Umbauqh |
| 5,993,412 A | 11/1999 | Deily et al. |
| 6,053,895 A | 4/2000 | Kolberg et al. |
| 6,083,197 A | 7/2000 | Umbauqh |
| 6,123,684 A | 9/2000 | Deboer et al. |
| 6,224,577 B1 | 5/2001 | Dedola et al. |
| 6,319,224 B1 | 11/2001 | Stout et al. |
| 6,398,763 B1 | 6/2002 | Richardson et al. |
| 6,506,177 B2 | 1/2003 | Landau |
| 6,558,348 B2 | 5/2003 | Parsons |
| 6,673,035 B1 | 1/2004 | Rice et al. |
| 6,752,780 B2 | 6/2004 | Stout et al. |
| 6,939,319 B1* | 9/2005 | Anstead .............. A61M 5/30 604/68 |
| 6,942,638 B1 | 9/2005 | Quinn |
| 7,235,063 B2 | 6/2007 | D'Antonio et al. |
| 7,341,575 B2 | 3/2008 | Rice et al. |
| 7,442,182 B2 | 10/2008 | Landau et al. |
| 7,618,393 B2 | 11/2009 | Bingham et al. |
| 7,699,802 B2 | 4/2010 | Steinway et al. |
| 9,700,675 B2 | 7/2017 | Capello et al. |
| 2001/0031945 A1 | 10/2001 | Haar et al. |
| 2001/0031956 A1 | 10/2001 | Drevik |
| 2002/0022806 A1 | 2/2002 | Witowski |
| 2002/0068921 A1 | 6/2002 | McWethy |
| 2002/0188251 A1 | 12/2002 | Staylor et al. |
| 2003/0065286 A1 | 4/2003 | Landau |
| 2003/0109846 A1 | 6/2003 | Zinger et al. |
| 2003/0132547 A1 | 7/2003 | Heffernan et al. |
| 2003/0225368 A1 | 12/2003 | Landau et al. |
| 2004/0134563 A1 | 7/2004 | Rice et al. |
| 2004/0159364 A1 | 8/2004 | Landau et al. |
| 2005/0209553 A1* | 9/2005 | Landau .............. A61M 5/30 604/72 |
| 2006/0089593 A1 | 4/2006 | Landau et al. |
| 2006/0106362 A1 | 5/2006 | Pass et al. |
| 2007/0027428 A1 | 2/2007 | Bingham |
| 2007/0043319 A1 | 2/2007 | Kimmel |
| 2007/0118094 A1 | 5/2007 | Bingham et al. |
| 2007/0167907 A1 | 7/2007 | Deslierres et al. |
| 2007/0191762 A1 | 8/2007 | Quinn |
| 2008/0015512 A1 | 1/2008 | D'Antonio et al. |
| 2008/0281261 A1 | 11/2008 | Steinway et al. |
| 2009/0156992 A1 | 6/2009 | Landau |
| 2009/0247940 A1 | 10/2009 | Williamson et al. |
| 2009/0318880 A1 | 12/2009 | Janish |
| 2010/0076374 A1 | 3/2010 | Landau et al. |
| 2010/0168662 A1 | 7/2010 | Bingham et al. |
| 2011/0129794 A1 | 6/2011 | Pauser |
| 2011/0257624 A1 | 10/2011 | Green |
| 2011/0319860 A1 | 12/2011 | Williamson et al. |
| 2013/0035634 A1 | 2/2013 | Cappello et al. |

FOREIGN PATENT DOCUMENTS

| | | |
|---|---|---|
| GB | 1 333 215 | 10/1973 |
| HK | 1200126 | 8/2017 |
| JP | 2007-534345 | 11/2007 |
| KR | 101052669 | 7/2011 |
| SU | 1210844 A1 | 2/1984 |
| WO | WO-95-03844 | 2/1995 |

(56) References Cited

FOREIGN PATENT DOCUMENTS

| WO | WO-97-036783    | 10/1997 |
| WO | WO-2002-005878  | 1/2002  |
| WO | WO-2004-041331  | 5/2004  |
| WO | WO-2004-010125  | 11/2004 |
| WO | WO-2006-009839  | 1/2006  |
| WO | WO-2006-106291  | 10/2006 |
| WO | WO-2006-118616  | 11/2006 |
| WO | WO-2007-146266  | 12/2007 |
| WO | WO-2008-063995  | 5/2008  |

OTHER PUBLICATIONS

International Search Report dated Oct. 11, 2007, for PCT Patent Application No. PCT/US2007/013744 filed on Jun. 12, 2007, three pages.

International Search Report dated Jul. 23, 2008, for PCT Patent Application No. PCT/US2007/84510 filed Nov. 13, 2007, six pages.

Supplementary Partial European Search Report dated Jul. 23, 2008, for EP Patent Application No. 05854705.0 filed Dec. 12, 2005, seven pages.

International Search Report dated Feb. 26, 2013, for PCT Patent Application No. PCT/US2012/049312.

International Search report dated Mar. 27, 2013, for PCT/US2012/069063 filed Dec. 12, 2012, 11 pages.

Extended European Search Report dated Aug. 15, 2015 for Corresponding European Application No. 12856712.0.

Chinese Office Action and Search Report dated Aug. 28, 2015 for Corresponding Chinese application No. 201280061865.8.

JP Office Action and Search Report dated Sep. 2, 2016 for JP application No. 2014-547359 corres. to PCT/US2012/069063; 9 pgs (with English Translation).

RU Office Action, dated Jan. 19, 2017, for RU application No. 2014-128599, 5 pages, (English Translation).

MX Office Action, dated Feb. 10, 2017, for MX application No. 2014-00653, 2 pages. (English Translation).

U.S. Appl. No. 15/235,797, Non-Final Office Action, dated Nov. 18, 2016, 32 pages.

U.S. Appl. No. 15/235,797, Notice of Allowance, dated Mar. 8, 2017, 24 pages.

* cited by examiner

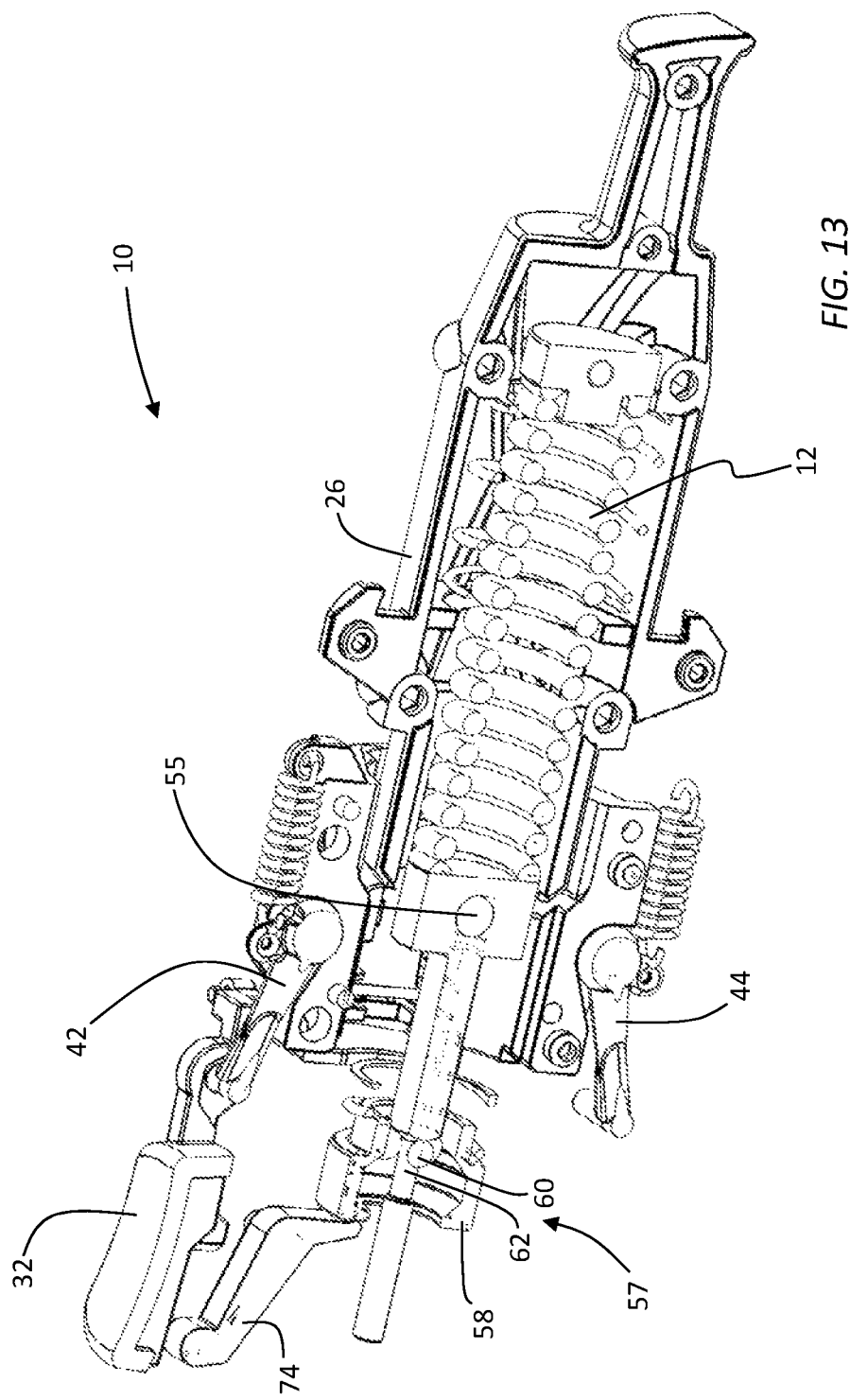

NEEDLE-FREE INTRADERMAL INJECTION DEVICE

RELATED APPLICATION DATA

This application is a continuation of U.S. patent application Ser. No. 15/235,797 filed on Aug. 12, 2016, which is a continuation of U.S. patent application Ser. No. 13/711,765 filed Dec. 12, 2012, entitled "Needle-Free Intradermal Injection Device," which claims priority to U.S. Provisional Patent Application No. 61/570,163, filed Dec. 13, 2011, which application is incorporated by reference herein in its entirety.

CONTRACTUAL ORIGIN

Certain embodiments disclosed herein were made the support of the United States Government. The United States Government has certain rights in this invention under Contract No. 200-2010-37152 between the United States Centers for Disease Control and Prevention and PharmaJet, Inc.

TECHNICAL FIELD

The embodiments disclosed herein relate generally to needle-free injection devices and methods of injecting serums, medicine, inoculants or other injectable fluid into the intradermal space of a human or animal.

BACKGROUND

The advantages of needle-free injection devices have been recognized for some time. Some of the advantages of needle-free devices and methods include the absence of a needle which can intimidate a patient and also present a hazard to healthcare workers. In addition, injection using a needle may increase the risk of cross-contamination between patients. Furthermore, with an injection device that employs a needle there is substantial risk of needle breakage in the tissue of a human or animal patient. The injection jet generated by a needle-free device is generally smaller in diameter than a hypodermic needle and thus in certain instances a needle-free injection is less painful than an injection provided by a hypodermic needle device.

Because of these and other advantages of needle-free injection many variations of pneumatic, electronic or spring activated needle-free injection devices have been designed to provide a single injection, or alternatively a series of injections to one or more patients. Most known needle-free injection devices operate by driving the injectable fluid through a fine nozzle with a powered piston to create a fine but high pressure jet of fluid that penetrates the skin. Needle-free injection devices are not inherently risk free. For example, it is possible if precautions are not taken, to cause a laceration as opposed to a proper injection with a needle-free device. In addition, it is critical to design a needle-free device with safety features substantially minimizing the risk of inadvertent triggering or injection.

Safety issues may involve the risk of accidental discharge of a needle-free device. Safety issue can become acute in association with devices that have exposed triggers or devices which include a ram or piston driving mechanism that can extend beyond the housing of the injector. The risk of using these types of devices is similar to the risks associated with the triggers on firearms. Thus, the inadvertent pressing of an exposed and armed trigger can cause the accidental or premature firing or triggering of the needle-free injection device.

One class of reliability issue with known needle-free injection devices involves difficulty delivering an entire preselected dosage of injectable liquid into the appropriate tissue of a patient. This situation can be exacerbated when the dosage is intended to be delivered shallowly, in the intradermal space for example. Dosage reliability issues have a broad spectrum of causes. One significant underlying cause is the difficulty encountered in the creation of a suitable jet or stream of fluid and introduction of this jet into or through the skin of a patient. Preferably, the jet will be a very fine jet that will impact a section of taught skin with much of the energy of the stream being used to penetrate the skin. The elasticity and permeability of a patient's skin can however vary with respect to other patients or across different locations on a patient's body. Another reliability issue concerns difficulty encountered efficiently and accurately pre-filling needle-free syringes to a selected dosage without significant waste of a potentially very limited supply of injectable fluid.

The embodiments disclosed herein are directed toward overcoming one or more of the problems discussed above.

SUMMARY

One embodiment disclosed herein is a needle-free injection device suitable for delivering a therapeutic substance into the intradermal space of a patient. The needle-free injection device includes a compressible main spring which can be compressed to place the needle-free injection device into an armed configuration. In addition, the device includes at least one and possibly two handles which are attached to the needle-free injection device such that the handle or handles may pivot between an open and a closed position. In addition, the device includes a linkage between one or each of the handles and the main spring. The linkage provides for the mainspring to be compressed into the armed configuration when the device handle or handles are moved from the open to the closed position.

The disclosed embodiments therefore uniquely include one or more handles attached to the needle-free injection device which provide for the compression of the main spring. The leverage necessary to compress a main spring which is suitably sized to deliver a needle-free injection places substantial stress on the hinges connecting the handles to the device. Therefore, the needle-free injection device may also include pivot hinges having upper and lower pivot studs and spatially separated radius surfaces. In use, the upper pivot stud is engaged with the upper handle and the lower pivot stud is engaged with the lower handle. The separate radius surfaces mate with a corresponding or matching surface on the upper and lower handles and provide additional support to a handle beyond that provided by the pivot stud. Device longevity and proper functioning is it promoted by providing both pivot studs and radius surfaces to support each handle. Typically, each handle will be supported by left and right pivot studs and left and right radius surfaces on each side of the device.

Certain embodiments of the needle-free injection device also include a sleeve engaged with the handle linkages and the main spring, which sleeve is caused to move or slide laterally with respect to the portions of the injection device housing the mainspring when the handle or handles are moved from the open position to the closed position. In an embodiment having two handles, the handles made generally be referred to as an upper and lower handle and in selected embodiments the upper and lower handle each have at least one linkage between the respective handle and the sleeve or main spring.

Disclosed embodiments also include a catch mechanism configured to engage the handles and hold each in the closed position. Furthermore the device may include a release button or release mechanism configured to release the closed handles and allow each handle to move to the open position. As noted below, safe usage is enhanced if the release button cannot under any circumstance also release energy stored in the main spring.

The needle-free injection device may include an injector tube housing the main spring and a hammer. During an injection, force stored in the main spring may be released to drive the hammer forward or toward the nozzle end of the syringe. The hammer is thus in contact with the plunger of the needle-free syringe and positioned to transfer energy from the main spring to the plunger causing a needle-free injection.

In certain embodiments the injector tube housing the main spring, hammer and associated apparatus can be caused to move laterally away from the front (syringe) end of the device when pressure is applied to a needle-free syringe prior to an injection. The syringe itself is attached to the injector tube in use and moves with the main spring, hammer and associated apparatus. As described in detail below, the respective movement between the injector tube and other elements of the needle-free injection device provides certain specific functional and safety advantages.

In particular, the needle-free injection device may include a skin tensioning spring configured to bias the injector tube toward the syringe end of the injection device. The disclosed devices will include an actuation button which, when the device is ready to be operated to deliver an injection, will be in mechanical communication with a hammer release. The actuation button therefore, in certain carefully controlled circumstances, causes the device to deliver a needle-free injection. Safe and effective functioning of the device can be enhanced by configuring the actuation button such that it cannot engage the hammer release unless the injector tube moved to a position fully away from the front end of the device.

In embodiments including a skin tensioning spring, the rearward movement of the injector tube and associated apparatus prior to injection is important for two distinct reasons. First, prior to an injection, the nozzle end of a needle-free syringe is placed against a patient's skin and the needle-free injection device is pressed toward the patient with sufficient force to compress the skin tensioning spring. This action, in conjunction with the specific shape of the nozzle end, causes the patient's skin to be appropriately tensioned to assure that a suitable injection is made. In addition, providing an actuation button that does not engage the hammer release mechanism unless the injector tube is moved to a position fully away from the front end of the device assures that an injection cannot be delivered in normal use unless the nozzle end of the needle-free syringe is placed against a patient's skin and the needle-free injection device is pressed forward with sufficient force properly tension the skin.

The disclosed device embodiments may be implemented with any type or configuration of hammer and hammer release apparatus. One representative type of hammer release includes one or more ball bearings housed within a ball lock which communicates with a notch defined within the exterior surface of the hammer. As noted above, the handles of the device may be opened from a latched configuration after use to compress the main spring by operating a release switch or button. It is important for safe used to assure that the handle release cannot also or inadvertently release the main spring and hammer. The disclosed embodiments accomplish this requirement by including a separate hammer release apparatus which may only be actuated by the actuation switch and then only when the device is properly positioned for the delivery of an injection as noted above.

Additional safety may be provided by including a retract button mechanically linked to the injector tube. The retract button may be configured to cause the injector tube to be locked in the forward position, toward the syringe end of the device, unless the retract button is depressed or otherwise activated. Thus, a user is substantially prohibited from accidentally placing the device into an injection configuration since the injector tube cannot be moved away from the syringe end of the device into the injection configuration described above unless the user deliberately and intentionally permits said movement by operating the retract button before or while applying enough pressure to a patient's skin with the nozzle end of the syringe to compress the skin tensioning spring.

Alternative embodiments disclosed herein include a needle-free injection system comprising a needle-free injection device substantially as described above. In addition a system will include at least one needle-free syringe. One disclosed needle-free syringe includes a syringe body having a nozzle at one end and a dose setting surface substantially opposite the nozzle. The syringe will also include a plunger body having a leading end, a seal and a hammer surface substantially opposite the leading end. In use, the plunger body is inserted into a dosage space defined with in the syringe such that the leading end of the plunger points toward the syringe nozzle. The dosage space is defined within the syringe between the nozzle opening and the plunger seal. A needle-free syringe may be sized and configured such that the dosage space has a select dosage volume when the plunger body is positioned within the syringe body and the dose setting surface and hammer surface of the plunger are coplanar. The needle-free syringe and plunger assembly may be provided to define any suitable dosage volume. For example, a dosage volume of 0.1 ml is suitable for the delivery of certain therapeutic substances into the intradermal space.

The needle-free syringe system may optionally further include a handle substantially opposite the plunger body, a separable shaft between the plunger body and the handle, and a break line defined in the separable shaft. In this alternative, the break line defines the hammer surface on the plunger body. In addition, the handle may include a plunger positioning surface which cooperates with the hammer surface to position the plunger body in a needle-free syringe body such that the dose setting surface and hammer surface are coplanar. The plunger positioning surface may define a hole providing a clearance for any nub formed in the hammer surface upon separation of the plunger body from the handle at the break line. Alternatively or in addition to the above, the end of the hammer operatively positioned adjacent to the plunger may cause the hammer surface and dose setting surface to become coplanar when a syringe is loaded into the armed device.

Alternative embodiments disclosed herein include methods of operating a needle-free injection device or system, to arm the device, deliver an injection or perform other operations. For example the disclosed methods may be implemented to deliver an injection into the intradermal space of a patient. Disclosed methods include providing a needle-free injection device substantially as described above and moving the handle or handles from the open position to the closed position thereby compressing the device mainspring from an un-armed to an armed position. The method may further include loading a needle-free syringe into the device and subsequently releasing energy stored in the mainspring to drive a syringe plunger forward causing an injection.

As noted above, selected embodiments of the disclosed devices include certain features which promote safe and effective operation. Accordingly, the disclosed methods may include the steps of activating a retract button to unlock an injector tube or similar apparatus, thus allowing the injector tube, syringe and associated apparatus to be moved with respect to other device elements. The method may further include applying force against a patient's skin at the nozzle end of the needle-free syringe thereby causing the injector tube to move laterally with respect to the handles or other stationary elements of the injector. As noted above, this step properly tensions the patient's skin for an injection and moves the actuation mechanism of the needle-free injector into an injection position. Then and only then, an actuation button may be activated to release the energy stored in the mainspring to drive the syringe plunger forward causing an injection.

BRIEF DESCRIPTION OF THE DRAWINGS

FIG. 13 is a perspective cross sectional view of selected internal structures of a needle-free injection device, after the main spring has been compressed and locked, but before the compression of the skin tensioning spring.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figure 1:
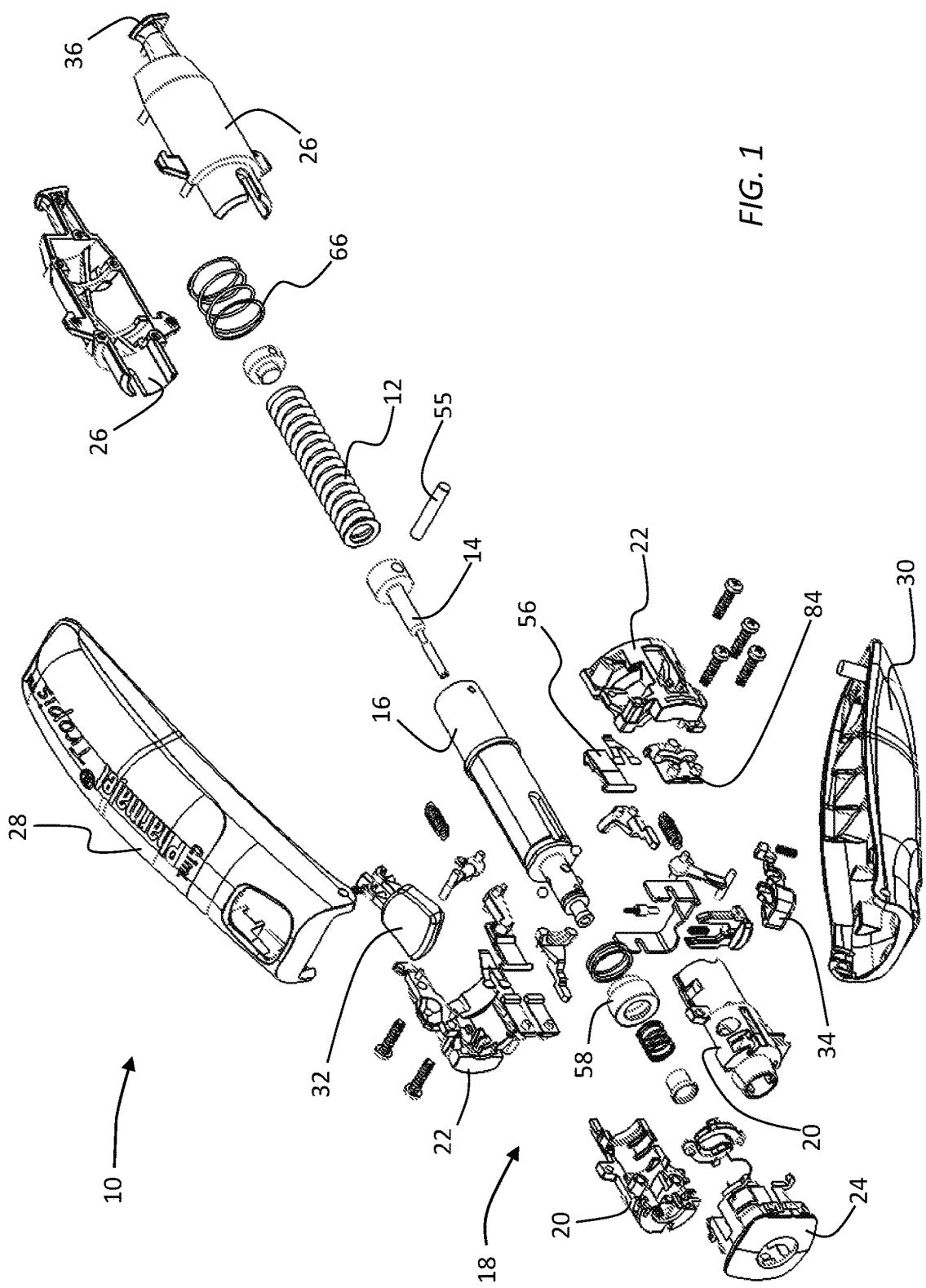
FIG. 1 is an exploded perspective view of a needle-free injection device.

FIG. 1 is an exploded perspective view of a needle-free injection device 10. The needle-free injection device 10 includes an injection power source, in particular, a main spring 12 which may be compressed to store energy for subsequent release to power an injection. The main spring 12 is engaged with a hammer 14 such that when energy stored within the main spring 12 is released, the hammer 14 is driven toward and into contact with the plunger of a needle-free syringe providing for a needle-free injection as described in detail below. The main spring 12, hammer 14 and associated apparatus may be housed within an injector tube 16.

The needle-free injection device 10 also includes a core 18 which may alternatively be referred to as the injector device body. The core 18 may include, but is not limited to a pivot sleeve 20. The needle-free injection device 10 also includes a return sleeve 22, syringe receptacle 24 and latch and release sleeve 26. The structure and functioning of each of these elements is described in detail below.

It may also be noted from FIG. 1 that the needle-free injection device 10 includes at least one handle, and in the illustrated embodiment, two handles, which may be referred to as an upper handle 28 and lower handle 30. In the illustrated embodiment the handles 28, 30 are attached to the pivot sleeve 20. At least one handle associated with the injector device or alternatively both the upper handle 28 and lower handle 30 may be moved from an open position to a closed position by a user to provide the force necessary to compress, store energy and thereby arm the main spring 12 for an injection.

Also shown on FIG. 1 are three control buttons or switches associated with the device including an actuation button 32, retract button 34 and release button 36. Other operational buttons could be provided in alternative embodiments.

Figure 2:
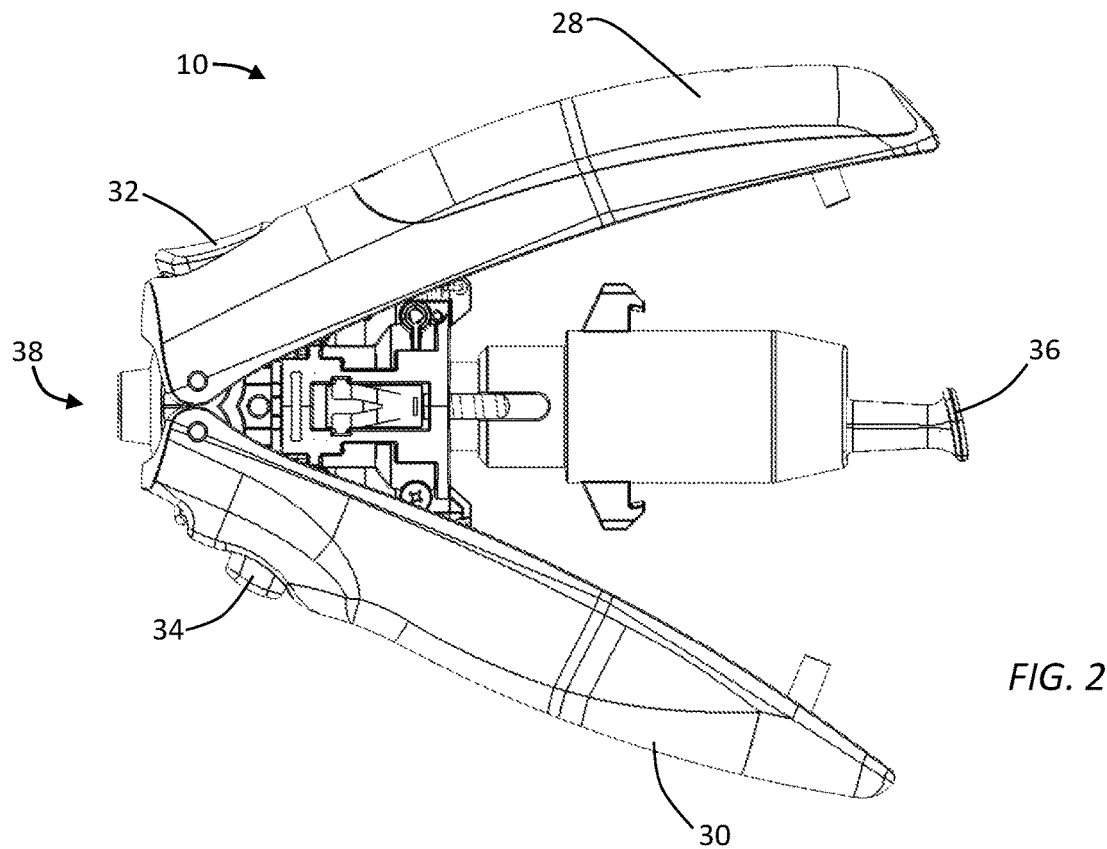
FIG. 2 is a side elevation view of a needle-free injection device in an open and ready to charge configuration.
Figure 3:
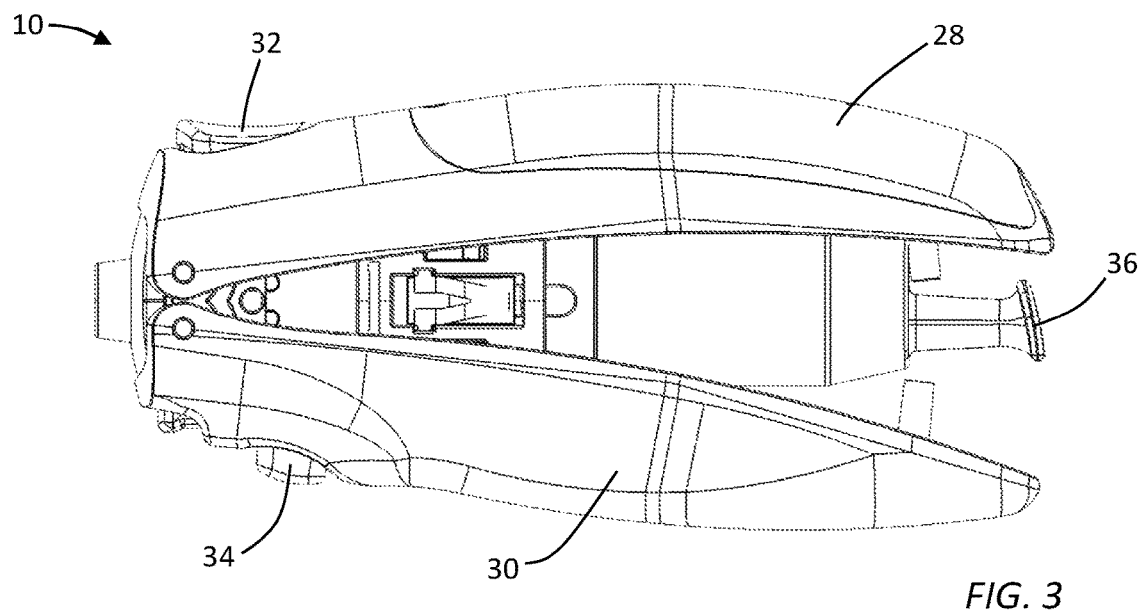
FIG. 3 is a side elevation view of a needle-free injection device in the process of being charged.
Figure 4:
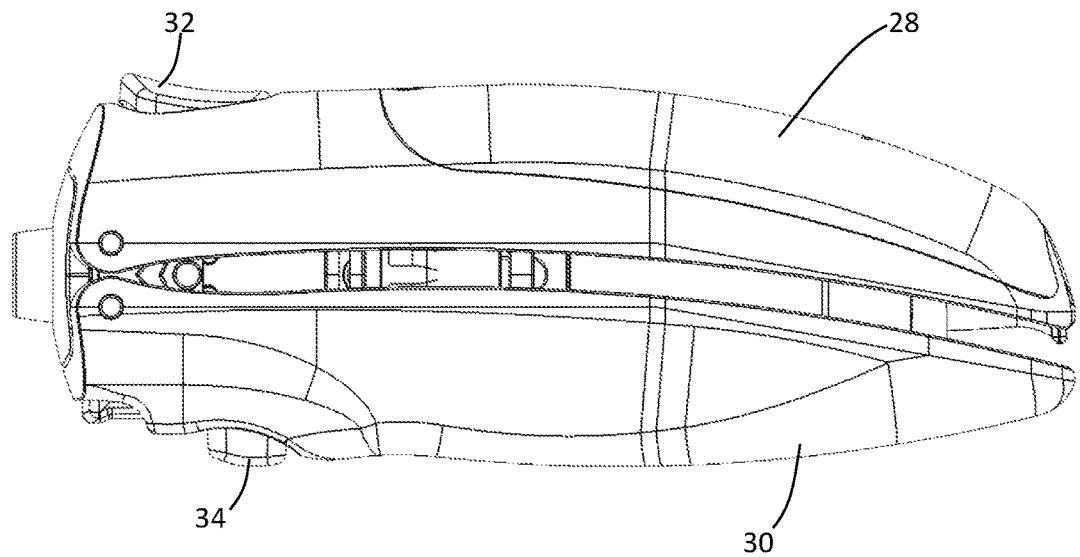
FIG. 4 is a side elevation view of a needle-free injection device in a fully charged configuration.
Figure 5:
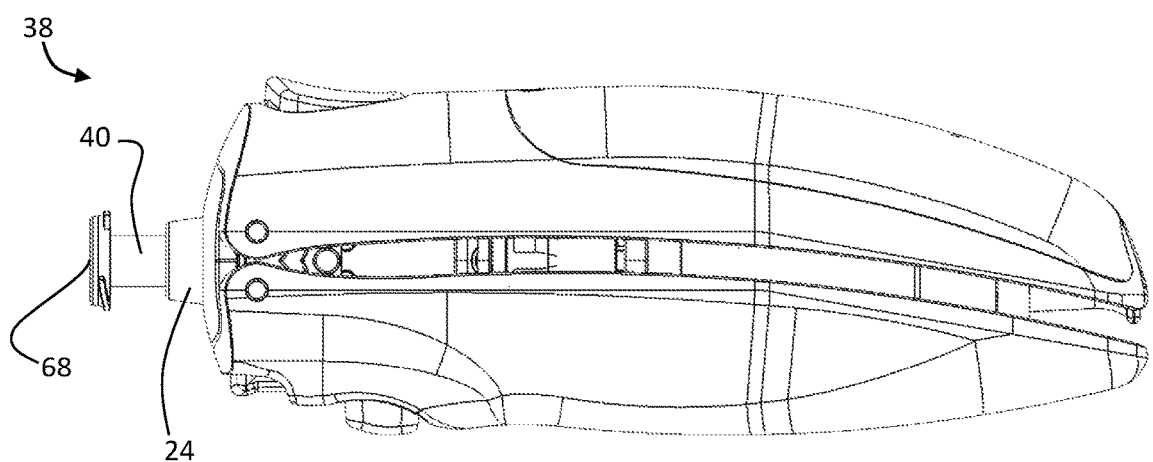
FIG. 5 is a side elevation view of a needle-free injection device in a fully charged configuration with a needle-free syringe inserted therein.

FIGS. 2-5 show external side elevation views of the needle-free injection device 10 with the handles 28, 30 and other elements in various operational states. In particular, FIG. 2 shows the handles 28, 30 in the fully open position. In the FIG. 2 position the main spring 12 is extended or de-compressed and ready to be charged for an injection. FIG. 3 illustrates the handles 28, 30 in a partially closed configuration, for example as the handles would be positioned during the process of compressing the main spring 12, but prior to full compression. FIG. 4 shows the handles 28, 30 fully closed and latched. In the FIG. 4 configuration the main spring 12 is fully charged and ready to provide for an injection as described in detail below. FIG. 5 illustrates the charged needle-free injection device 10 with a needle-free syringe 40 inserted into the syringe receptacle 24 at the syringe end 38 of the needle-free injection device 10.

Figure 6:
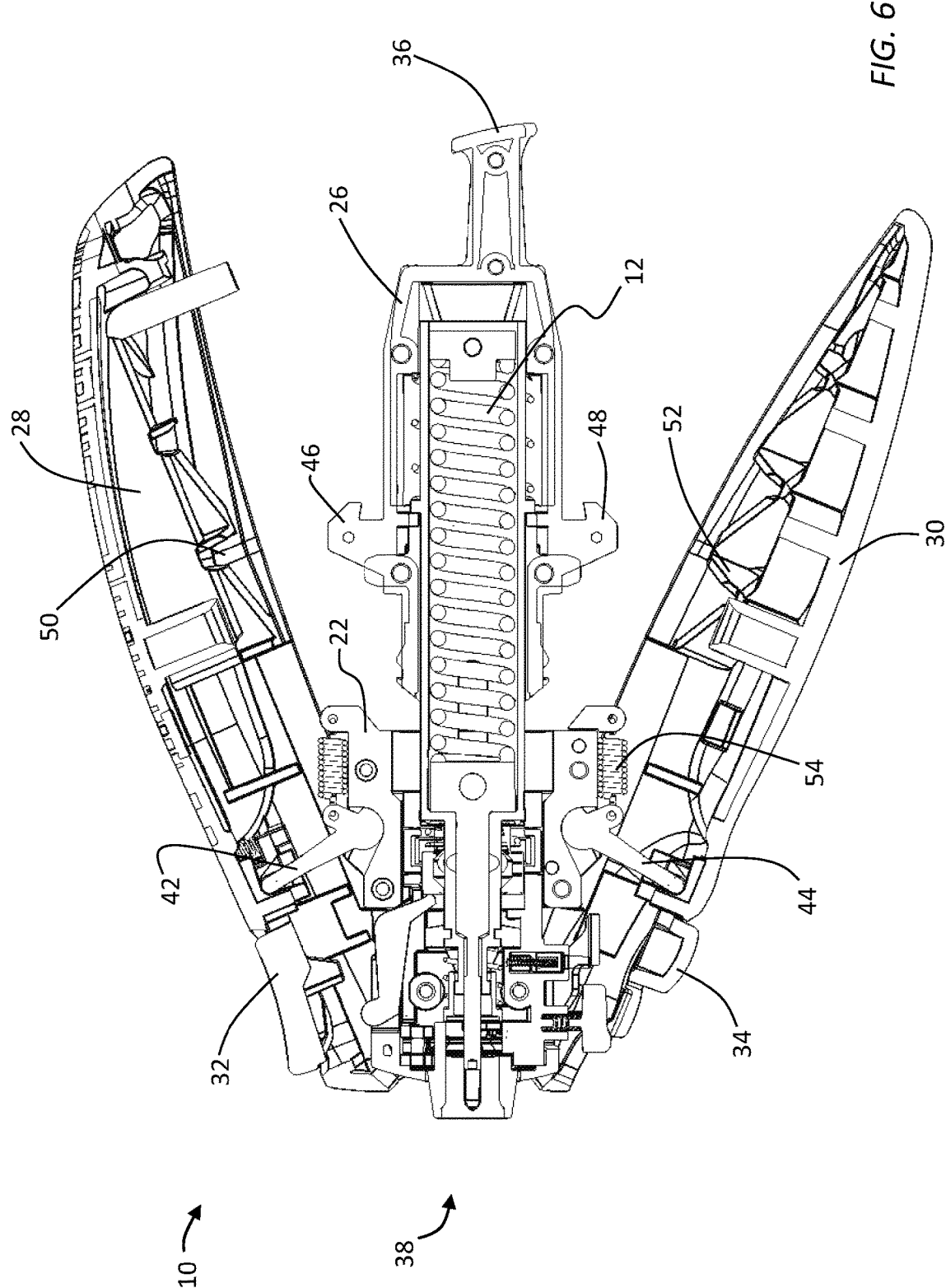
FIG. 6 is a side cross sectional view of a needle-free injection device in an open and ready to charge configuration.
Figure 7:
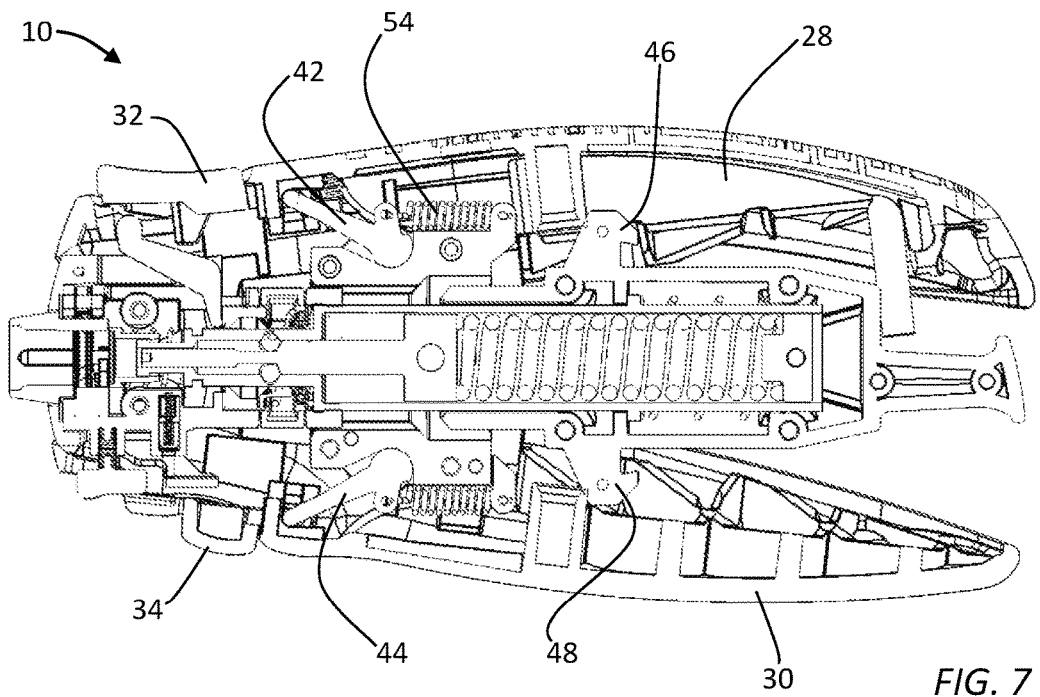
FIG. 7 is a side cross sectional view of a needle-free injection device in the process of being charged.
Figure 8:
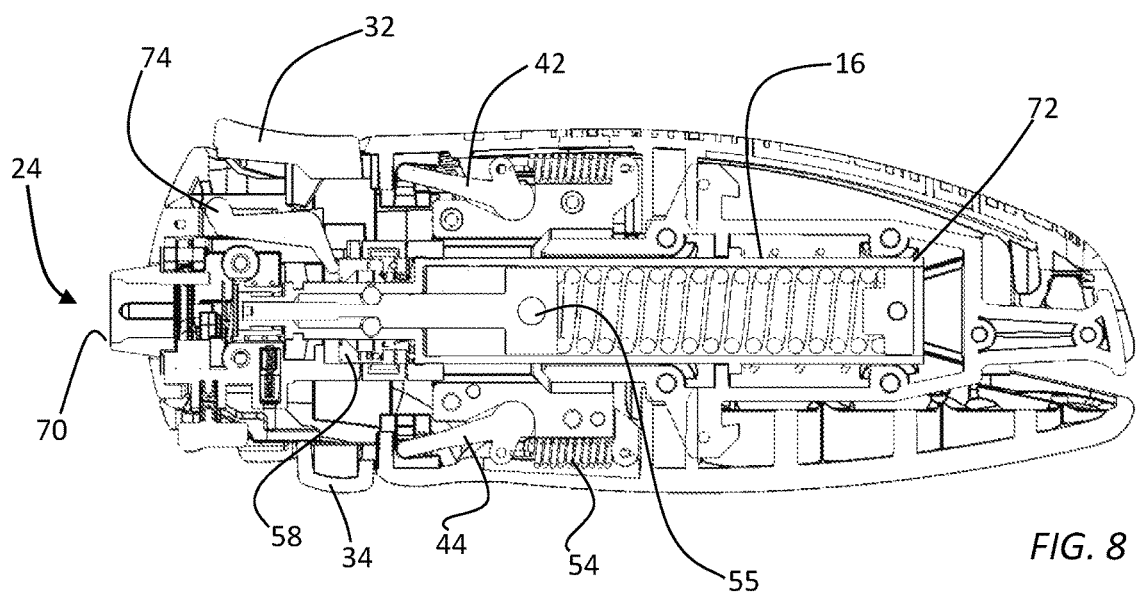
FIG. 8 is a side cross sectional view of a needle-free injection device in a fully charged configuration.

FIGS. 6-14 show various cross-sectional views of the needle-free injection device 10 in selected operational states. FIGS. 6-14 may thus be referred to in order to more fully understand the elements and operational subsystems providing enhanced convenience, safety, durability, and effectiveness to the user of a needle-free injection device 10. In particular, FIG. 6 is a cross-sectional view of the needle-free injection device 10 with the handles 28, 30 in a fully open position. As noted above, in the FIG. 2 or FIG. 6 position, the main spring 12 is in a decompressed and ready to charge state. As may be observed on FIG. 6, each of the handles 28, 30 engages with a linkage 42, 44 respectively which in turn is engaged with the return sleeve 22. In the embodiment illustrated in FIG. 6, the upper handle 28 is engaged with an upper linkage 42 and the lower handle 30 is engaged with a lower linkage 44. Both the upper and lower linkage 42, 44 have a bearing surface which engages a corresponding surface on the return sleeve 22. As may be noted by comparing FIG. 6 with FIG. 7 (which shows the handles 28, 30 in a partially closed position) as the handles 28, 30 are closed, the linkages 42, 44 force the return sleeve 22 away from the syringe end 38 of the device. As the return sleeve 22 is forced toward the rear of the device by the handles 28, 30 and linkages 42, 44, the main spring 12 is compressed. FIG. 7 shows the main spring 12 in a partially compressed state, FIG. 8 shows the main spring 12 in a fully compressed state. It is important to note that the particular configuration of handles, linkages, a return sleeve and main spring illustrated in the figures is not limiting. Other mechanical configurations could be used to implement the functionality of handle closure acting to compress the main spring and charging an alternative embodiment of needle-free injection device.

Returning to FIG. 6, it may be noted that the latch and release sleeve 26 includes an upper latching member 46 and a lower latching member 48. Each handle 28, 30 has a corresponding latching surface with the upper handle 28 having an upper latching surface 50 and the lower handle 30 having a lower latching surface 52. In use, the upper latching member 46 engages the upper latching surface 50 when the handles 28, 30 are in a fully closed position. The lower latching member 48 and lower latching surface 52 engage in the same way. Thus, when the handles 28, 30 are closed to the fully closed configuration illustrated in FIG. 8, the handles 28, 30 are latched shut. The handles 28, 30 when placed in the FIG. 8 closed position are configured to remain latched shut until such time as the release button 36 is depressed, moving the latch and release sleeve 26 forward a short distance with respect to the injector tube 16 which causes the latch members 46, 48 and latch surfaces 50, 52 to disengage returning the needle-free injection device 10 to the FIG. 6 configuration. As will be described below, the release button 36 cannot operate to release the main spring 12 under any circumstance providing used safety.

It may also be noted by comparison of FIGS. 6, 7 and 8 that as the return sleeve 22 is moved away from the syringe end 38 of the needle-free injection device 10, one or more return springs 54 are extended. Return spring extension biases the return sleeve 22 toward the syringe end 38 of the needle-free injection device 10 such that the return sleeve 22 is motivated to slide forward when the handles 28, 30 are opened.

Figure 11:
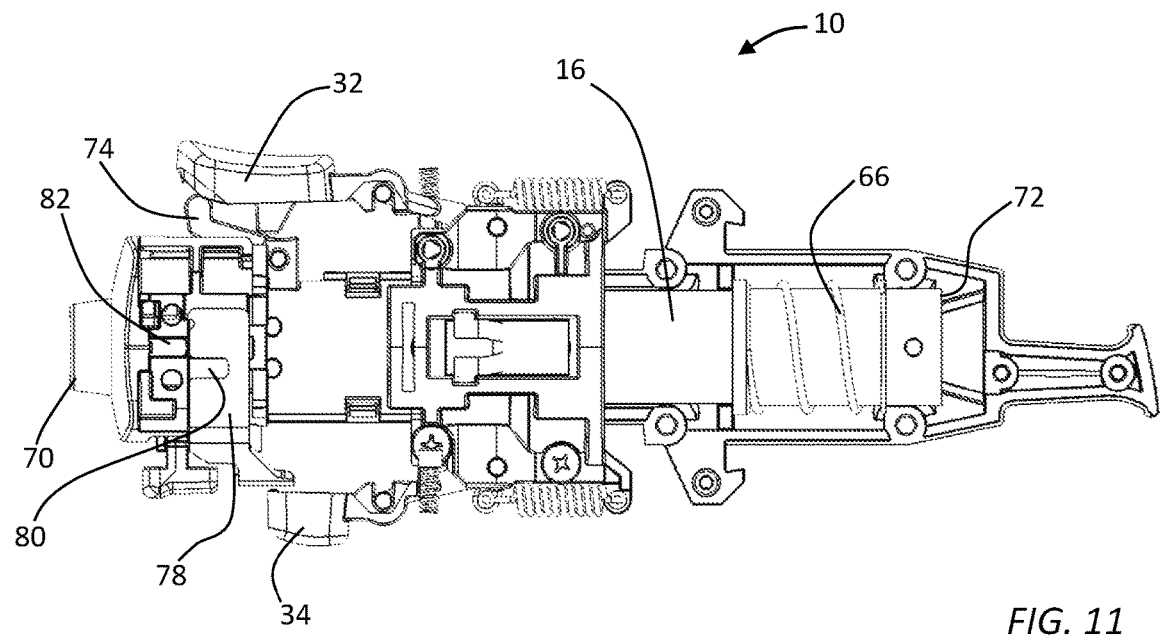
FIG. 11 is a side cross sectional view of selected internal structures of a needle-free injection device, prior to unlocking the injector tube with the retract button.
Figure 14:
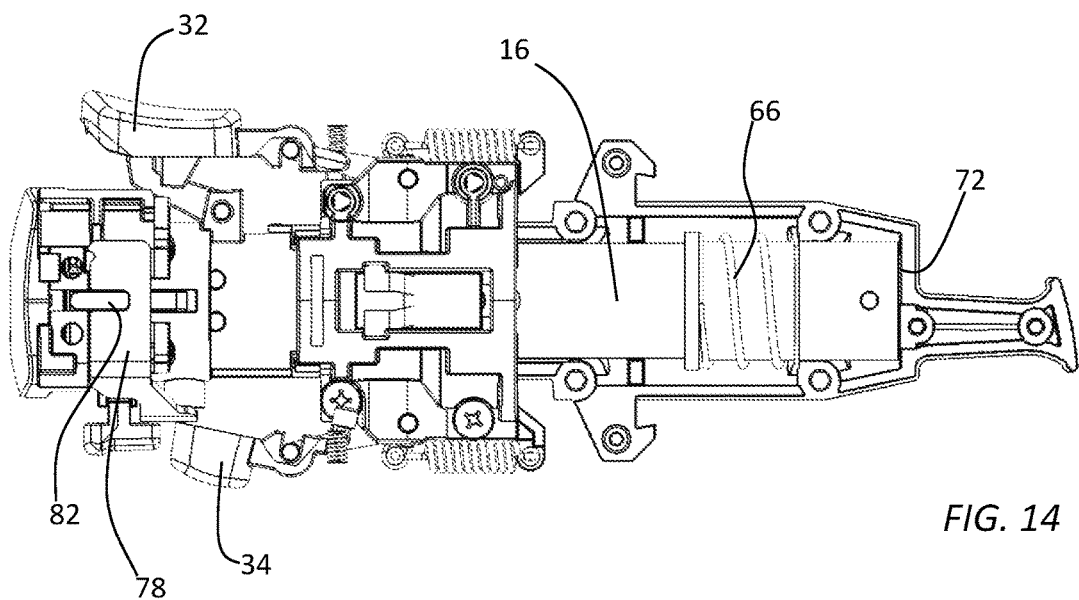
FIG. 14 is a side cross sectional view of selected internal structures of a needle-free injection device after compression of a skin tensioning spring immediately prior to an injection.
Figure 12:
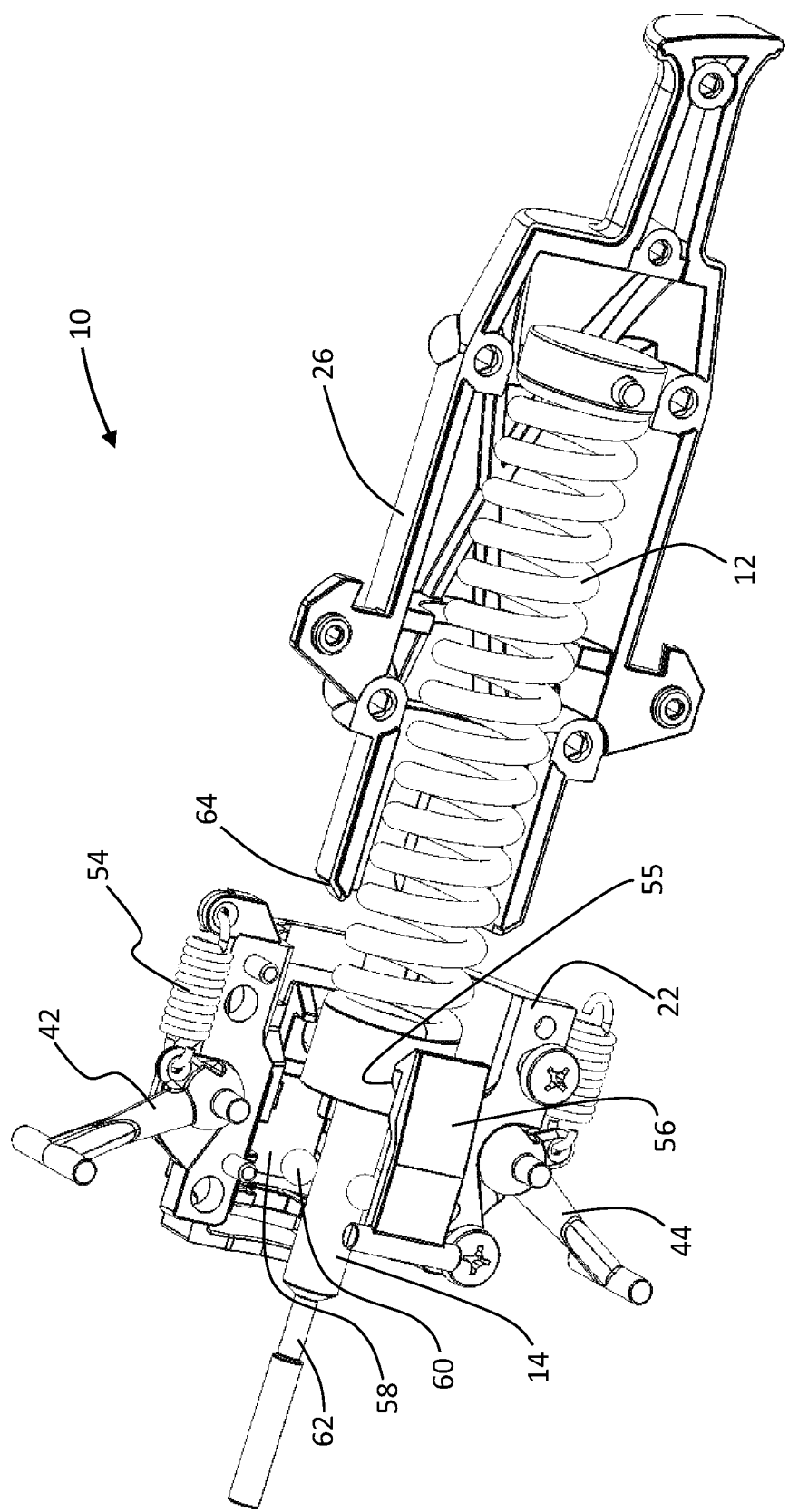
FIG. 12 is a perspective cross sectional view of selected internal structures of a needle-free injection device, prior to arming the device for an injection.

FIGS. 11 and 12 are side elevation and perspective cross-sectional views of the needle-free injection device 10 in the handle open/ready to charge position of FIG. 6. FIGS. 13 and 14 are perspective and front elevation cross sectional views of needle-free injection device 10 after the main spring has been compressed (FIG. 13) and after a skin tensioning spring has also been compressed, as described in detail below (FIG. 14). In the FIG. 11-14 views, the handles 28, 30 and various other structures have been removed to provide a more detailed view of the return sleeve 22, main spring 12, hammer 14 and associated apparatus. In particular, FIG. 12 shows the engagement of the upper linkage 42 and lower linkage 44 with corresponding surfaces on the return sleeve 22 such that closing the handles 28, 30 causes the linkages 42, 44 to force the return sleeve 22 and hammer away from the syringe end 38 of the needle-free injection device 10 thereby compressing the main spring 12.

As also shown in the FIG. 12 view, side posts 55 extend from the portion of the hammer 14 adjacent the main spring 12. The side posts could be independent structures, or as shown in FIG. 1 a pin extending through the hammer. The side posts 55 are engaged with clips 56 when the return sleeve is retracted. Thus, the clips 56 bind the hammer 14 to the return sleeve 22 when the needle-free injection device 10 is in an open and ready to charge configuration and as the device is charged. As best shown in FIG. 13, as the needle-free injection device 10 nears and reaches the fully charged position, a hammer release 57 including ball bearings 60 associated with a ball lock sleeve 58 drop into a notch 62 defined in the hammer. Thus, the ball lock sleeve 58 and associated apparatus lock the hammer 14 in a charged position at a time when the clips 56 are still engaged with the side posts 55. When the handles 28, 30 are fully closed, the clips 56 move into engagement with the ramped front surface 64 of the return sleeve to be forced away from the side posts 55 and therefore to allow for subsequent clearance between the side posts and the return sleeve as the device is fired.

Figure 9:
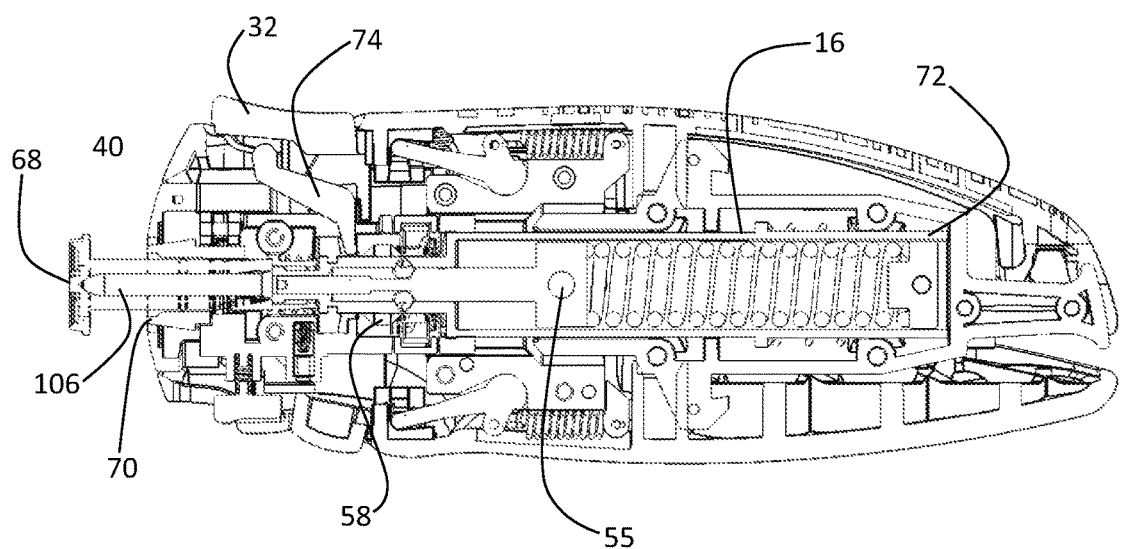
FIG. 9 is a side cross sectional view of a needle-free injection device in a fully charged configuration with a needle-free syringe inserted therein, after compression of a skin tensioning spring immediately prior to an injection.

As is best shown in FIGS. 5, 8 and 9, when the needle-free injection device 10 is placed in a fully charged configuration and the handles 28, 30 are locked; a needle-free syringe 40 may be placed into the syringe receptacle 24. As described in detail below, the needle-free injection device 10 includes various safety systems to assure that an inadvertent injection is not made when the needle-free syringe 40 is placed into the syringe receptacle 24 or at any other time.

In particular, it may be noted by comparing FIG. 8 with FIG. 9 that the combined elements of the syringe receptacle 24, a needle-free syringe 40, the hammer 14, main spring 12 and ball lock sleeve 60 may all be moved, in association with the injector tube 16 housing the main spring and hammer, laterally away from the syringe end of the pivot sleeve 20 and associated handles. A skin tensioning spring 66 is provided which biases against the lateral rearward movement of the injector tube 16. See for example FIG. 11 where the skin tensioning spring 66 is not compressed and FIG. 14 where the skin tensioning spring 66 has been compressed.

The rearward movement of the injector syringe receptacle 24, needle-free syringe 40, hammer 14, main spring 12 and ball lock sleeve 60 is important for two distinct reasons. First, prior to an injection, the nozzle end 68 of a needle-free syringe 40 is placed against a patient's skin and the needle-free injection device 10 is pressed toward the patient with sufficient force to compress the skin tensioning spring 66. This action, in conjunction with the specific shape of the nozzle end 68, causes the patient's skin to be appropriately tensioned to assure that a suitable injection is made. It may be noted from a comparison of FIG. 8 and FIG. 9 or FIG. 11 with FIG. 14 that both the forward end 70 of the syringe receptacle 24 and the rear end 72 of the injector tube 16 slide backward (away from the syringe end 38 of the device) with respect to other elements of the needle-free injection device 10 as the skin tensioning spring is compressed. This functionality provides for proper skin tensioning as described above and also is linked to device safety as described below.

Figure 10:
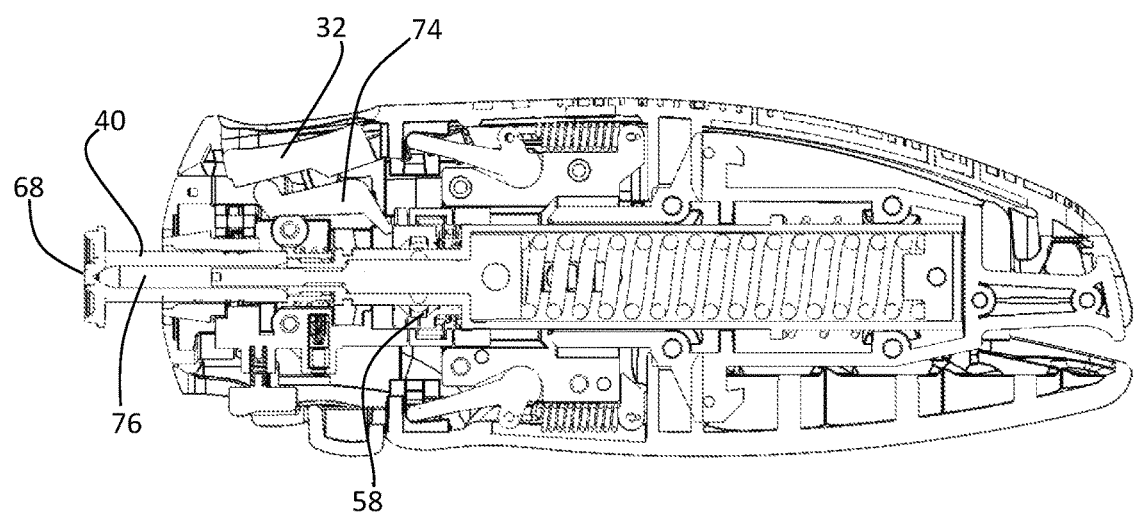
FIG. 10 is a side cross sectional view of a needle-free injection device after an injection.

The needle-free injection device 10 is provided with an actuation button 32 which in certain instances releases the main spring to provide an injection. As shown in FIG. 9 and FIG. 14, when the needle-free injection device 10 is fully armed, the skin tensioning spring 66 is fully compressed and the injector tube and the elements within or attached to the injector tube are moved or slid fully away from the syringe end of the device as described above, the actuation button 32 communicates with the ball lock sleeve 58 through activation linkage 74. As shown in FIG. 10, when the actuation button 32 is depressed in this fully charged and armed configuration, the activation linkage 74 forces the ball lock sleeve 60 toward the rear of the device a short distance freeing the ball bearings 60 from the notch 62 allowing the main spring 12 to rapidly decompress, forcing the hammer 14 into contact with the plunger 76 of the needle-free syringe 40. As shown in FIGS. 6 and 7, however, the activation linkage 74 is not positioned in physical communication with the actuation button 32 until such time as the injector tube 16 and associated apparatus have been moved fully toward the rear of the needle-free injection device 10 by skin tensioning pressure on the nozzle end 68 of the needle-free syringe 40. Thus, the needle-free injection device 10 cannot be activated and an injection cannot be delivered in normal use unless the nozzle end 68 of the needle-free syringe 40 is placed against a patient's skin and the needle-free injection device 10 is pressed forward with sufficient force to compress the skin tensioning spring 66 and thereby properly tension the skin.

Additional safety is provided by the retract button 34 and associated apparatus. As is most readily seen in FIGS. 11 and 14, the retract button 34 communicates with a safety collar 78 having a notch 80 defined therein. The notch 80 corresponds with a tab 82 extending from an exterior surface of the syringe receptacle 24. As noted above, the syringe receptacle 24, injector tube 16, hammer 14 and syringe 40 may all be made to collectively slide or otherwise move toward the rear of the needle-free injection device 10 when appropriate skin tension is applied to the nozzle end 68 of the syringe 40. The tab 82 interferes with the safety collar 78 preventing rearward motion of the above assemblies until such time as the retract button 34 is depressed. Thus, in normal use, even though the main spring may be compressed, the device cannot be placed into a firing or injection-enabled configuration without first depressing the retract button 34. As noted above, the actuation button 32 cannot be engaged with the ball lock sleeve 60 until the injector tube 16 has been moved into a firing or injection configuration. Accordingly, a very high degree of safety is provided by the cooperation of the retract button 34 and actuation button 32 and associated assemblies. The device can not be accidentally placed into a firing position because of the retract button and the device can not be fired until it is intentionally placed into a firing position.

Figure 15:
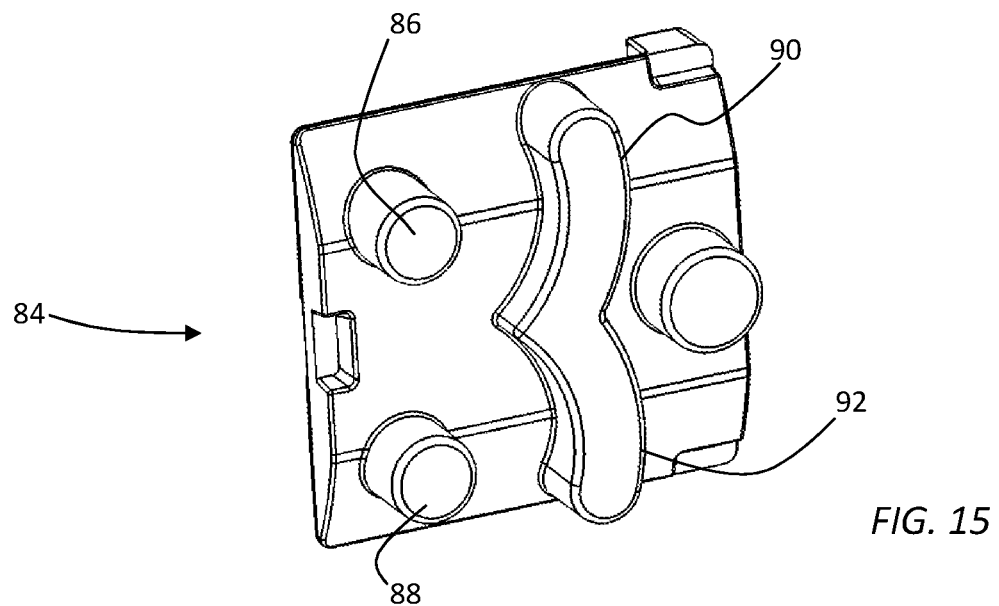
FIG. 15 is a perspective view of a pivot plate.

In certain embodiments the handles 28, 30 are fabricated from a plastic or other injection molded material. The handles 28, 30 experience substantial force when closed to compress the main spring 12 and charge the needle-free injection device 10. Accordingly, effective needle-free injection device 10 operation and longevity may be enhanced by providing a hinge which more fully supports handle pivot operation when compared to traditional pivot pins. FIG. 15 is a detailed perspective view of a pivot plate 84, one of which is located on each side of the device to support and provide for suitable pivoting of the upper and lower handles. Each pivot plate 84 includes an upper pivot stud 86 and lower pivot stud 88 which receive and support corresponding holes in the upper and lower handles 28, 30 providing for pivoted handle articulation. The pivot plates 84 also include upper and lower radius surfaces 90, 92, respectively. The upper and lower radius surfaces 90, 92 are configured to mate with a corresponding surface on the inside of each handle 28, 30 to provide support to the handle as it is move from an open to a closed position. Together, the pivot studs 86, 88 and upper and lower radius surfaces 90, 92 provide each handle 28, 30 with significantly enhanced support when compared to a simple pivot pin type attachments.

Figure 16A:
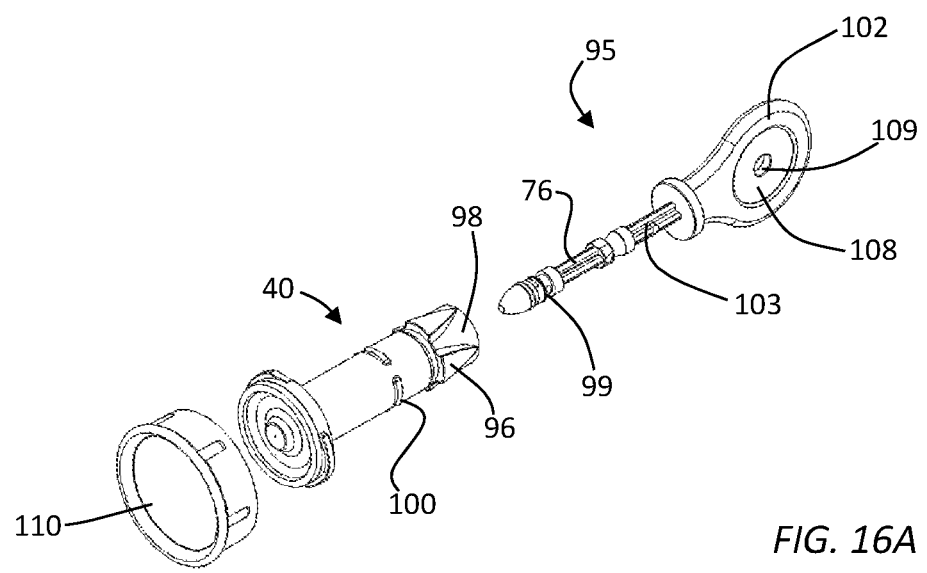
FIG. 16A is an exploded perspective view of a syringe, handle and plunger system.
Figure 16B:
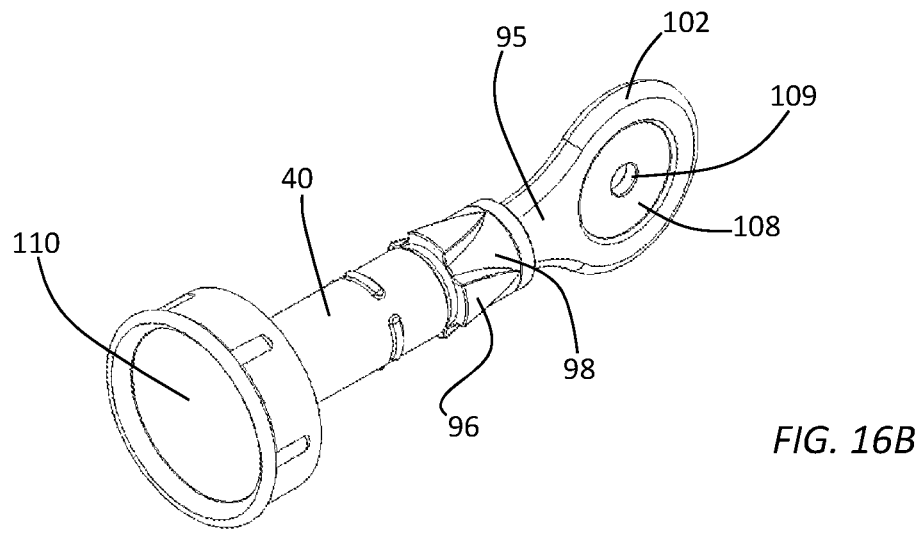
FIG. 16B is a perspective view of the syringe, handle and plunger system.
Figure 16C:
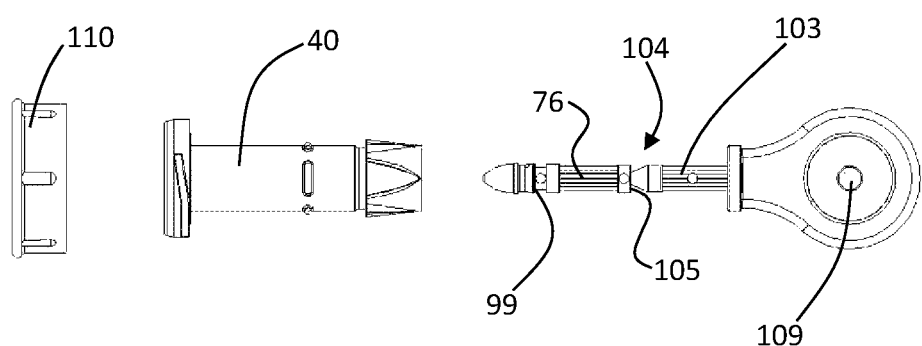
FIG. 16C is an exploded side elevation view of the syringe, handle and plunger system.

FIGS. 16A-16C include several views of a needle-free syringe 40 and syringe plunger system 94 showing certain enhancements. In particular, the needle-free syringe 40 may include at least two raised surfaces 96 defining at least one orientation channel 98 on the body of the needle-free syringe, typically at the trailing end. The orientation channel 98 is sized and configured to engage with corresponding syringe orientation guides associated with the syringe receptacle 24. Thus, a user may install a needle-free syringe 40 by sliding one or more orientation channels 98 over corresponding orientation guides until the pawls or another engagement mechanism engage with the syringe. Therefore, a syringe may be installed and locked for use without requiring the syringe body to be twisted as is necessary with conventional bayonet or screw type syringe mounts. The needle-free syringe 40 may also include visual indicia 100 which are illustrated as small raised portions but which could be implemented with any visually observable marker. In use, the visual indicia are placed in a visually identifiable position relative to or concealed by the forward end 70 of the syringe receptacle 24 thereby providing visual confirmation that a syringe 40 is properly installed.

It may be convenient to remotely prepare multiple needle-free syringes 40 for use with the needle-free injection device 10. For example, one operator could be loading needle-free syringes with an injectable fluid while another operator installs the needle-free syringes into the device and performs injections. Remote filling to a proper pre-determined dosage is facilitated by providing a plunger system 94 which includes a plunger body 76 and a seal 99 (See FIGS. 16A and 16C) sized to fit in fluid-tight engagement with the interior chamber of the syringe, thereby defining a fluid receiving dosage space within the needle-free syringe 40. As shown in FIG. 16, the plunger system 94 also may include a handle 102. The handle 102 may be conveniently separated from the plunger body 76 at a break line 104 defined in a separable shaft 103 between the plunger body and handle. In use the handle 102 and separable shaft 103 are typically broken away from the plunger body at the break line 104 after the syringe is filled, but before it is loaded into a device 10. Upon removal of the handle 102 and separable shaft 103, the trailing end of the plunger body 76 defines a hammer surface 105 which engages with the hammer 14 during an injection.

As shown in FIG. 9, the interior portion of the syringe 40 defines a dosage space 106 within the interior walls of the syringe between the nozzle and the plunger seal 99. This dosage space may be sized and configured to have a pre-selected injectable fluid dosage volume when the plunger body 76 is positioned within the syringe such that the hammer surface 105 is placed in a pre-defined spatial relationship with a dose setting surface 107 on the trailing edge of the syringe, substantially opposite the nozzle 68 (see FIG. 17A-17C). For example, the dosage space 106 may be sized to have a specific volume, for example 0.1 ml, when the hammer surface 105 is coplanar with the dose setting surface 107.

As shown in FIG. 9, the hammer 14 may be used to automatically position the plunger body 76 such that the hammer surface 105 and dose setting surface 107 are coplanar. For example, the syringe and plunger assembly may be loaded into the needle-free injection device 10 with the hammer surface 105 extending slightly beyond the dose setting surface 107 and the location of the corresponding end of the hammer 14 causes these two surfaces to become coplanar. It may also be noted that the leading edge of the hammer 14 may include a recess which provides clearance for any extension or nub remaining beyond the hammer surface 105 when the separable shaft 103 is removed from the plunger body 76 at the break line 104.

Proper dose setting may also be accomplished in the absence of the needle-free injection device 10 by using the plunger positioning surface 108 associated with the handle 102 to manually position the hammer surface 105 to be coplanar with the dose setting surface 107. The plunger positioning surface 108 may, as shown in FIG. 16, include a hole 109 which provides clearance for any extension or nub formed in the hammer surface 105 upon separation of the plunger body from the handle at the break line. Thus, during a remote filling operation, a user may insert the plunger body 76 and attached handle assembly 95 fully into a needle-free syringe 40 such that the leading end of the plunger body 76 is in contact with the interior surface of the nozzle. The nozzle may be placed in fluid communication with a supply of injectable material. The handle may be then be used to withdraw the plunger body 76 to a point where the hammer surface 105 extends beyond the dose setting surface 107 of the syringe, thereby slightly over-filling the syringe. The handle and separable shaft may then be removed at the break line 104 and the hammer surface and dose setting surface 107 made to be coplanar (thus precisely setting the selected dosage) by pressing upon the hammer surface with the plunger positioning surface 108 of the handle. The foregoing operation may be performed while the nozzle is continuously maintained in sterile fluid communication with an injectable substance supply, thus minimizing waste.

Figure 17A:
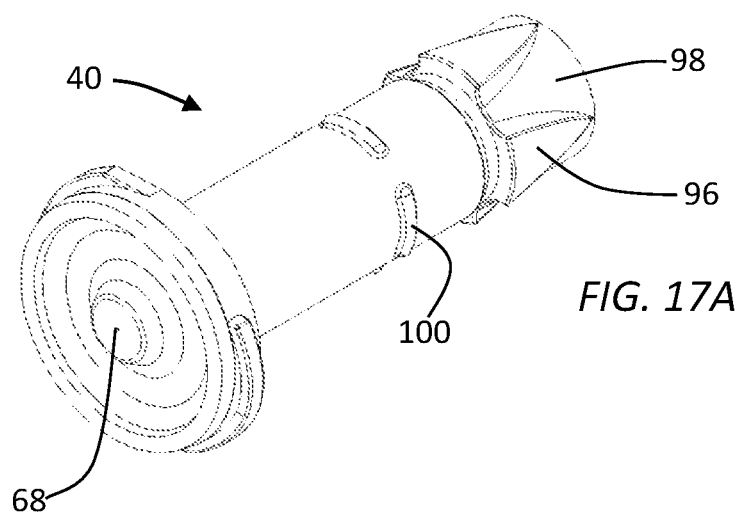
FIG. 17A is a perspective view of a needle-free syringe.
Figure 17B:
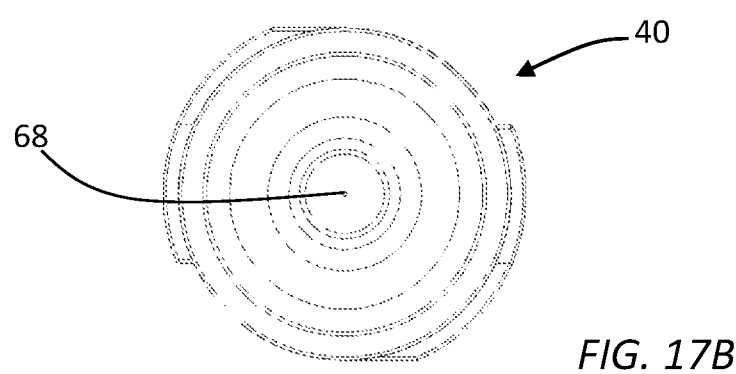
FIG. 17B is a front (nozzle end) view of the needle-free syringe.
Figure 17C:
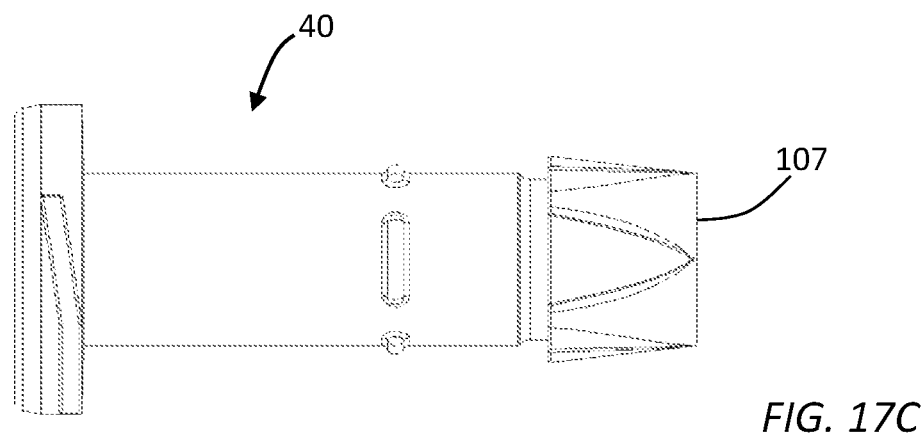
FIG. 17C is a side elevation view of the needle-free syringe.

Returning to FIG. 16 it may be noted that the needle-free syringe 40 may be provided with a cap 110 sized to engage the nozzle end of the syringe body. FIGS. 17A-17C include several alternative views of a needle-free syringe 40 as described herein.

Alternative embodiments include methods of charging, operating and filling a needle-free injector as described above. For example, one embodiment includes a method of arming a needle-free injection device comprising the steps of providing a needle-free injection device or system as disclosed above, moving one or more handles associated with the needle-free injection device from an open position to a closed position thereby compressing the main spring of the needle-free injection device from an un-armed to an armed position. The method may further include actuating a release to cause an injection.

Figure 18:
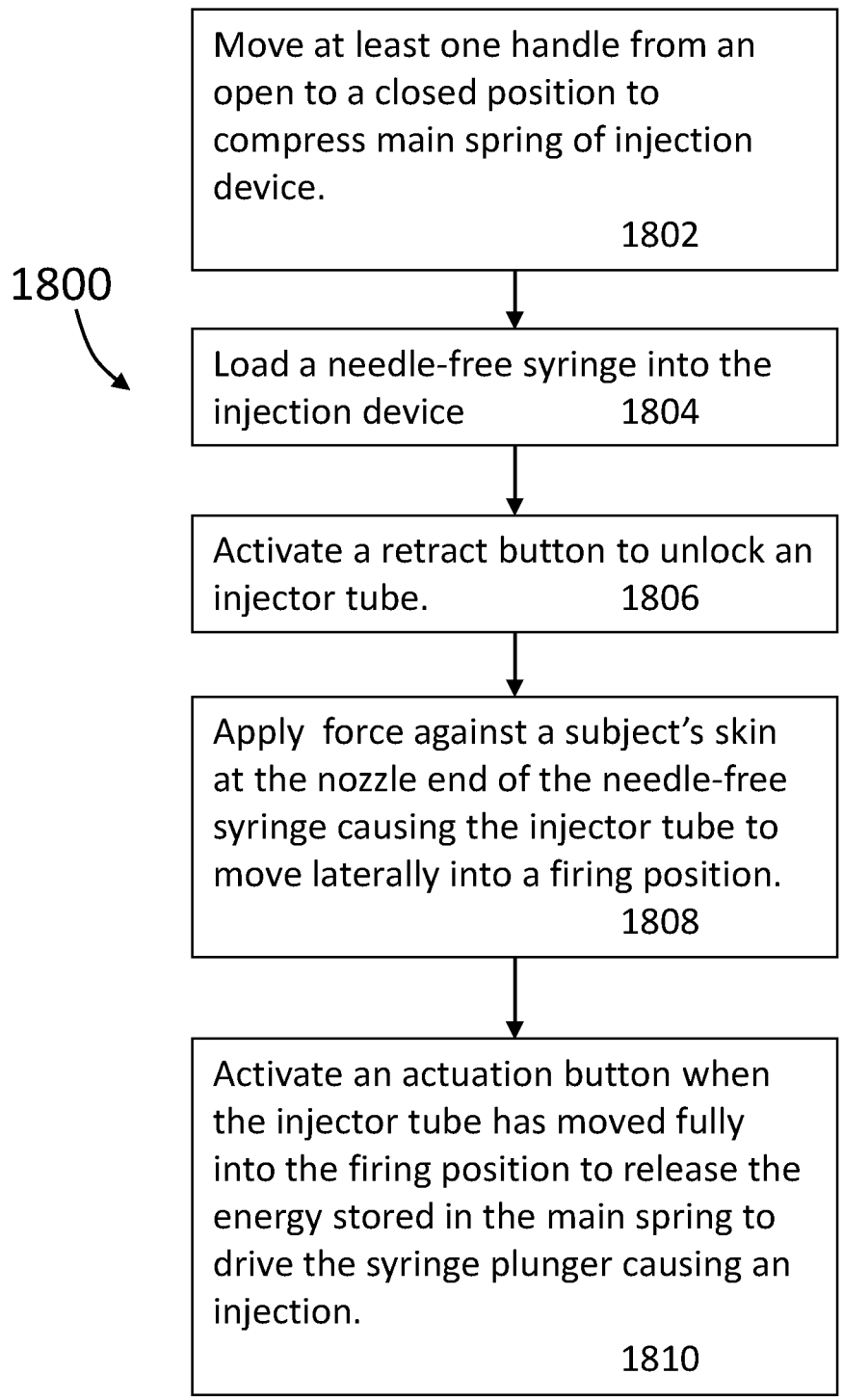
FIG. 18 is a flow chart representation of a method of delivering a needle-free injection.

As more particularly shown in the flow chart of FIG. 18, a method 1800 may include the steps of moving at least one handle from an open to a closed position to compress the main spring of injection device (Step 1802). Next, a needle-free syringe may be loaded into the injection device (Step 1804). A user may then activate a retract button to unlock an injector tube within the device, allowing the device to be positioned for an injection (Step 1806). As noted above, the injector cannot be fired at this point in time because the firing or injection enabling mechanism is not in mechanical communication with actuation button. Immediately prior to injection, the user may apply force against a subject's skin at the nozzle end of the needle-free syringe, causing the injector tube to move laterally into an injection firing position. (Step 1808). As noted above movement into the firing/injection position may be prohibited unless the retract button has been depressed. Then, with the patient's skin properly tensioned, the user may activate an actuation button to release the energy stored in the main spring to drive the syringe plunger causing an injection (Step 1810).

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the embodiments described herein have been particularly shown and described with reference to a number of possible variations, it would be understood by those skilled in the art that changes in the form and details may be made to various components or elements without departing from the spirit and scope of the embodiments and that the various embodiments disclosed herein are not intended to act as limitations on the scope of the claims. All references cited herein are incorporated in their entirety by reference.

What is claimed is:

1. A needle-free injection device comprising:
    an injector body defining a syringe end of the injector body;
    a first handle attached to the injector body such that the first handle pivots between an open and a closed position and remains attached to the injector body during an injection;
    a main spring positioned within the injector body;
    a return sleeve engaged with the main spring;
    a first linkage between the first handle and the return sleeve, wherein the first linkage causes the return sleeve to move away from the syringe end of the injector body when the first handle is moved from the open position to the closed position, thereby compressing the main spring; and
    a return spring biasing the return sleeve toward the syringe end of the injector body.

2. The needle-free injection device of claim 1 further comprising:
    a second handle; and
    a second linkage between the second handle and the return sleeve.

3. The needle-free injection device of claim 2 further comprising at least one pivot hinge between the injector body and the first and second handles, the pivot hinge comprising:

two pivot studs with a first pivot stud being engaged with the first handle and a second pivot stud being engaged with the second handle; and two radius surfaces with a first radius surface mating with a corresponding surface on the first handle and a second radius surface mating with a corresponding surface on the second handle.

4. The needle-free injection device of claim 2 further comprising a latch and release sleeve to engage the first and second handles and hold each handle in the closed position.

5. The needle-free injection device of claim 4 further comprising a release button to release the handles from engagement with the latch and release sleeve and allow each handle to move to the open position.

6. The needle-free injection device of claim 1 further comprising:
a hammer engaged with the main spring; and
a hammer release in mechanical communication with an actuation button, wherein actuation of the actuation button when the main spring is compressed can permit the main spring to decompress, driving the hammer toward the syringe end of the injector body.

7. The needle-free injection device of claim 6 wherein the hammer release comprises one or more ball bearings housed within a ball lock.

8. The needle-free injection device of claim 6 further comprising:
a side post extending from the hammer; and
a clip extending from the return sleeve, wherein the clip binds the side post and the hammer to the return sleeve when the handle is not in a fully closed position.

9. The needle-free injection device of claim 8 wherein the clip is disengaged from the side post and the hammer when the handle is in a fully closed position.

10. A method of operating a needle-free injection system comprising:
providing a needle-free injection device comprising:
an injector body defining a syringe end of the injector body;
a first handle attached to the injector body such that the first handle pivots between an open and a closed position and remains attached to the injector body during an injection;
a main spring positioned within the injector body;
a return sleeve engaged with the main spring;
a first linkage between the first handle and the return sleeve;
moving the first handle from the open position to the closed position causing the first linkage to cause the return sleeve to move away from the syringe end of the injector body thereby compressing the main spring;
providing a return spring biasing the return sleeve toward the syringe end of the injector body; and
moving the handle from the closed position to the open position, permitting the return spring to move the return sleeve toward the syringe end of the injector body.

11. The method of claim 10 further comprising:
providing a second handle attached to the injector body such that the second handle pivots between an open and a closed position;
providing a second linkage between the second handle and the return sleeve; and
moving the first handle and the second handle from the open position to the closed position causing the first linkage and the second linkage to cause the return sleeve to move away from the syringe end of the injector body thereby compressing the main spring.

12. The method of claim 11 further comprising:
providing at least one pivot hinge between the first handle, the second handle and the pivot hinge, said pivot hinge comprising;
two pivot studs with a first pivot stud being engaged with the first handle and a second pivot stud being engaged with the second handle; and
two radius surfaces with a first radius surface mating with a corresponding surface on the first handle and a second radius surface mating with a corresponding surface on the second handle.

13. The method of claim 11 further comprising:
providing a latch and release sleeve; and
engaging the first and second handles with the latch and release sleeve to hold each handle in the closed position.

14. The method of claim 13 further comprising:
providing a release button in mechanical communication with the latch and release sleeve; and
actuating the release button to disengage the handles from the latch and release sleeve and allow each handle to move to the open position.

15. The method of claim 10 further comprising:
providing a hammer engaged with the main spring;
providing a hammer release in mechanical communication with an actuation button; and
actuating the actuation button when the main spring is compressed to permit the main spring to decompress, driving the hammer toward the syringe end of the injector body.

16. The method of claim 15 wherein the hammer release comprises one or more ball bearings housed within a ball lock.

17. The method of claim 15 further comprising:
providing a side post extending from the hammer;
providing a clip extending from the return sleeve; and
binding the side post and the hammer to the return sleeve with the clip when the handle is not in a fully closed position.

18. The method of claim 17 further comprising disengaging the clip from the side post and the hammer when the handle is in a fully closed position.

* * * * *